United States Patent [19]

Gessner

[11] Patent Number: 5,712,416
[45] Date of Patent: Jan. 27, 1998

[54] PREPARATION OF BENZOQUINONES BY OXIDATION OF PHENOLS

[75] Inventor: Thomas Gessner, Heidelberg, Germany

[73] Assignee: BASF Aktiengesellschaft, Ludwigshafen, Germany

[21] Appl. No.: 562,639

[22] Filed: Nov. 27, 1995

Related U.S. Application Data

[63] Continuation of Ser. No. 360,368, Dec. 21, 1994, abandoned.

[30] Foreign Application Priority Data

Dec. 21, 1993 [DE] Germany .................. 43 43 667.6

[51] Int. Cl.⁶ .................. C07C 46/02; C07C 46/04; C07C 46/06; C07C 46/08
[52] U.S. Cl. .................. 568/31; 568/338; 568/357; 568/361; 568/362; 568/371; 568/363
[58] Field of Search .................. 568/377, 31, 338, 568/357, 361, 362, 363

[56] References Cited

FOREIGN PATENT DOCUMENTS

| | | |
|---|---|---|
| 0 564 930 | 10/1993 | European Pat. Off. . |
| 0 568 806 | 11/1993 | European Pat. Off. . |
| 2 655 985 | 6/1991 | France . |
| 2 138 931 | 2/1973 | Germany . |
| 2427606 A1 | 1/1976 | Germany . |
| 3107201 | 9/1982 | Germany . |
| 3302498 A1 | 7/1984 | Germany . |
| 4029198 C2 | 3/1992 | Germany . |

OTHER PUBLICATIONS

"Catalytic Oxidations of Hydroquinones and 1,2-Dephenylhydrazine in the Presence of (Dibenzo [b,i][1,4,8,11] tetraazacyclotetradecinato)–cobalt(II)" in *Inorganica Chemica Acta*, vol. 144, pp. 1–3, 1988. By Kazunori Sakata, et al.
Japanese Docket Number JP 127,937/1974. Dated Dec. 7, 1974. English Abstract thereof.
Meunier et al., translation of FR 2 655 985, Jun. 1991.
Park et al., translation of "Saturated and Unsaturated –Azamacrocyclic Complexes (M=CO$^{3+}$, FE$^{3+}$, and MN$^{3+}$) Catalyzed Oxidation of Hindered Phenols by Molecular Oxygen Under Borohydride", Journal of the Korean Chemical Society, vol. 37, No. 7, 1993, pp. 648–654.
Inorganica Chemica Acta, vol. 144, pp. 1–3, 1988, Sakata et al.
CA Abstract 120: 163573 CA, Park et al, J. Korean Chem. Soc. (1993), 37(7), 648–654.
Jaeger et al., Z. Chem. (1985), 25(12), 4456.
White et al., Macromolecules, vol. 23, 1990.

*Primary Examiner*—Jeffrey C. Mullis
*Attorney, Agent, or Firm*—Oblon, Spivak, McClelland, Maier & Neustadt, P.C.

[57] ABSTRACT

Process for preparing benzoquinones by oxidation of phenols in the presence of a diluent and of an oxygen-transferring catalyst which contains a heavy metal ion bound in a complex, wherein oxygen, hydrogen peroxide, a compound which liberates hydrogen peroxide, an organic hydroperoxide, a percarboxylic acid or peroxomonosulfuric acid or salts thereof are used as oxidizing agent, and wherein the oxygen-transferring catalyst is from the class of iron, manganese or chromium tetraaza[14]annulenes.

10 Claims, No Drawings

PREPARATION OF BENZOQUINONES BY OXIDATION OF PHENOLS

This application is a Continuation of application Ser. No. 08/360,368, filed on Dec. 21, 1994, now abandoned.

The present invention relates to a novel process for preparing benzoquinones by oxidizing phenols in the presence of a diluent and of an oxygen-transferring catalyst which contains a heavy metal ion bound in a complex.

DE-A 3 302 498 discloses the oxidation of 2,3,6-trimethylphenol to 2,3,5-trimethyl-p-benzoquinone. Oxygen is used as oxidizing agent, and a cobalt-salcomine compound is used as catalyst. JP-A 127 937/1974 discloses that the same reaction can also be carried out with cobalt complexes of dimethylglyoxime, phthalocyanine or porphyrin. Furthermore, DE-A 4 029 198 describes this oxidation in the presence of a copper(II) halide catalyst.

Inorganica Chim. Acta. vol. 144, p. 1 to 3, 1988, describes the oxidation of various hydroquinones with air in the presence of (dibenzo[b,i][1,4,8,11]tetraazacyclotetradecinato)cobalt(II), -nickel(II) or copper (II).

It is an object of the present invention to provide a novel process for preparing benzoquinones which starts from the corresponding phenols or hydroquinones and provides the target products in a simple way in high yield and purity.

We have found that this object is achieved by preparing benzoquinones of the formula I

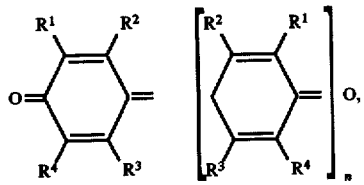

where $R^1$, $R^2$, $R^3$ and $R^4$ are, independently of one another, each hydrogen, $C_1$–$C_4$-alkyl, $C_1$–$C_4$-alkoxy, aryloxy, $C_1$–$C_4$-alkylsulfonyl, arylsulfonyl, hydroxysulfonyl, hydroxyl or halogen, and n is 0 or 1, by oxidizing a phenol of the formula II

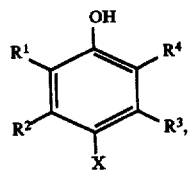

where X is hydrogen or hydroxyl, and $R^1$, $R^2$, $R^3$ and $R^4$ each have the abovementioned meanings, in the presence of a diluent and of an oxygen-transferring catalyst which contains a heavy metal ion bound in a complex, which takes place advantageously when oxygen, hydrogen peroxide, a compound liberating hydrogen peroxide, an organic hydroperoxide, a percarboxylic acid or peroxomonosulfuric acid or salts thereof are used as oxidizing agent, and the oxygen-transferring catalyst is from the class of iron, manganese or chromium tetraaza[14] annulenes.

All the alkyl groups occurring in the abovementioned formulae I and II can be either straight-chain or branched.

Examples of suitable $R^1$, $R^2$, $R^3$ and $R^4$ are methyl, ethyl, propyl, isopropyl, butyl, isobutyl, sec-butyl, tert-butyl, methoxy, ethoxy, propoxy, isopropoxy, butoxy, isobutoxy, sec-butoxy, phenoxy which is unsubstituted or substituted 1 to 3 times by $C_1$–$C_4$-alkyl, $C_1$–$C_4$-alkoxy or halogen, such as 2-, 3- or 4-methylphenoxy, 2-, 3- or 4-methoxyphenoxy, 2-, 3- or 4-chlorophenoxy, 2,4-dimethylphenoxy, 2,4-dimethoxyphenoxy or 2,4-dichlorophenoxy, methylsulfonyl, ethylsulfonyl, propylsulfonyl, isopropylsulfonyl, butylsulfonyl, phenylsulfonyl which is unsubstituted or substituted 1 to 3 times by $C_1$–$C_4$-alkyl, $C_1$–$C_4$-alkoxy or halogen, or fluorine, chlorine or bromine.

If the benzoquinones of the formula I have hydroxysulfonyl radicals and are in the form of a salt, suitable counter ions are metal or ammonium ions. Metal ions are, in particular, the lithium, sodium or potassium ions. Ammonium ions mean for the purpose of the invention either unsubstituted or substituted ammonium cations. Examples of substituted ammonium cations are monoalkyl-, dialkyl-, trialkyl-, tetraalkyl- or benzyltrialkylammonium cations or cations derived from nitrogen-containing five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl generally means in this connection straight-chain or branched $C_1$–$C_{20}$-alkyl which may be substituted by hydroxyl groups and/or interrupted by oxygen atoms.

Sodium and potassium ions should be emphasized.

A procedure for preparing benzoquinones of the formula I where n is 0 is preferred.

Also preferred is a procedure for preparing benzoquinones of the formula I where $R^1$, $R^2$, $R^3$ and $R^4$ are, independently of one another, each hydrogen, $C_1$–$C_4$-alkyl or hydroxysulfonyl.

A particularly preferred procedure is one for preparing benzoquinones of the formula I where $R^1$, $R^2$, $R^3$ and $R^4$ are, independently of one another, each hydrogen or methyl.

Also particularly preferred is a procedure for preparing benzoquinones of the formula I where $R^1$ and $R^3$ are each hydroxysulfonyl and $R^2$ and $R^4$ are each hydrogen.

A very particularly preferred procedure is one for preparing benzoquinones of the formula I where $R^1$, $R^2$ and $R^3$ are each methyl and $R^4$ is hydrogen.

Suitable catalysts which transfer oxygen and contain a heavy metal ion bound in a complex are from the class of iron, manganese or chromium tetraaza[14]annulenes.

The heavy metal ions as a rule have 2 or 3 charges.

Compounds of this type are described, for example, in DE-A 2 427 606.

They have, for example, the formula III

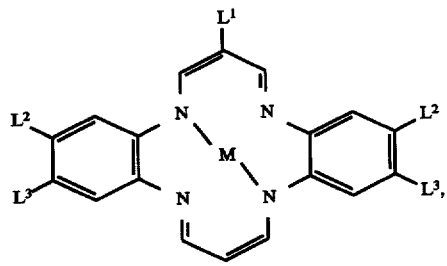

where $L^1$ is hydrogen, $C_1$–$C_8$-alkyl which is unsubstituted or substituted by hydroxysulfonyl, carboxyl, amino, mono- or di-$C_1$–$C_4$-alkylamino, ammonium, mono-, di- or tri-$C_1$–$C_4$-alkylammonium or benzyldi-$C_1$–$C_4$-alkylammonium, or chlorine, $C_1$–$C_4$-alkoxy, phenyl which is unsubstituted or substituted by hydroxysulfonyl, carboxyl, amino, mono- or di-$C_1$–$C_4$-alkylamino, ammonium, mono-, di- or tri-$C_1$-$C_4$-alkylammonium or benzyldi-$C_1$-$C_4$-alkylammonium, phenylazo which is unsubstituted or substituted by hydroxysulfonyl, carboxyl, amino, mono-or di-$C_1$-$C_4$-alkylamino, ammonium, mono-, di- or tri-$C_1$-$C_4$-alkylammonium or benzyldi-$C_1$-$C_4$-alkylammonium, or $C_1$-$C_4$-alkoxycarbonyl, hydroxysulfonyl or
a radical of the formula

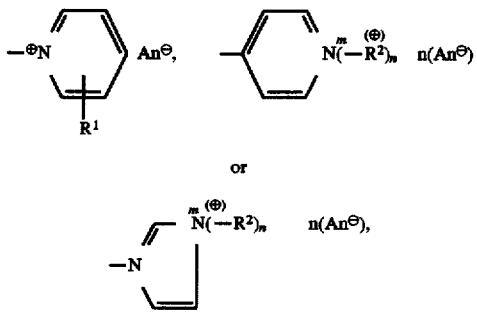

or

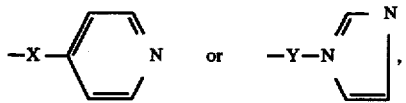

where
n is 0 or 1, $R^1$ is hydrogen, $C_1$-$C_4$-alkyl, carboxyl, $C_1$-$C_4$-alkoxycarbonyl or carbamoyl, $R^2$ is hydrogen or $C_1$-$C_4$-alkyl and $An^\ominus$ is the equivalent of an anion, $L^2$ and $L^3$, independently of one another, each hydrogen, methyl, hydroxysulfonyl, or $L^2$ and $L^3$ together are a fused-on benzene ring,
$L^4$ is the radical $L^1$ or a radical of the formula $$-X-\underset{}{\bigcirc}-N \quad \text{or} \quad -Y-N\underset{}{\bigcirc},$$

where Y is $C_1$-$C_8$-alkylene, and
M is iron, manganese, cobalt or chromium.

Examples of suitable anions are fluoride, chloride, bromide, iodide, bisulfate, sulfate, tetrafluoroborate, formate, acetate, propionate, mono-, di- or trichloroacetate, lactate, methoxyacetate, citrate, succinate, methylsulfonate, benzenesulfonate or 2- or 4-methylbenzenesulfonate.

These anions are also present when radicals substituted by ammonium, mono-, di- or trialkylammonium or benzyldialkylammonium occur in the radicals $L^1$ and/or $L^4$.

The use of iron tetraaza[14]annulenes as catalysts is particularly preferred.

Particular attention is drawn to the use of iron 5,14-dihydrodibenzo[b,i][5,9,14,18]tetraaza[14]annulene as catalyst, also known as (dibenzo[b,i][1,4,8,11] tetraazacyclotetradecinato)iron(II).

The catalysts can be used homogeneously or heterogeneously in solution. They may also be immobilized on a support material, e.g. silica gel or ion exchange resin.

The oxidizing agent used in the process according to the invention is oxygen, hydrogen peroxide, a compound liberating hydrogen peroxide, an organic hydroperoxide, a percarboxylic acid or peroxomonosulfuric acid or their salts.

Oxygen can be used either in pure form or in diluted form, e.g. as air. It is generally used in the gaseous state of aggregation. As a rule, 10 to 100 l of gaseous oxygen are fed in per 1 l of reaction mixture per hour.

Examples of suitable compounds liberating hydrogen peroxide are alkali metal perborates or percarbonates.

Examples of suitable organic hydroperoxides are cumene hydroperoxide and alkyl hydroperoxides, in particular tert-butyl hydroperoxide.

Examples of suitable percarboxylic acids are peracetic acid, m-chloroperbenzoic acid, magnesium bis (monoperoxyphthalate) hexahydrate or 1,12-diperoxydodecanedioic acid.

Preferred salts of peroxomonosulfuric acid are its alkali metal salts such as lithium, sodium or potassium peroxomonosulfate. The use of salts of peroxomonosulfuric acid, in particular sodium or potassium peroxomonosulfate, is preferred. It is also possible to use commercial mixtures of potassium peroxomonosulfate with potassium bisulfate and potassium sulfate.

The use of hydrogen peroxide, tert-butyl hydroperoxide or magnesium bis(monoperoxyphthalate) hexahydrate should be emphasized.

When hydrogen peroxide is used as oxidizing agent, it is, as a rule, used in the form of a 10–70% by weight aqueous solution.

The organic hydroperoxides are generally used in the form of an approximately 70% by weight aqueous solution.

Magnesium bis(monoperoxyphthalate) hexahydrate can be used in solid form, as aqueous solution or as aqueous suspension.

In some cases it may also be advantageous to carry out the process additionally in the presence of small amounts (generally up to 2 mol % based on the phenol II) of a compound which stabilizes the oxidizing agent, e.g. ethylenediaminetetraacetic acid, diethylenetriaminepentaacetic acid, nitrilotriacetic acid, β-alaninediacetic acid, isoserinediacetic acid, ethylenediaminetetra(methylenephosphonic acid), hexamethylenediaminetetra(methylenephosphonic acid), diethylenetriaminepenta(methylenephosphonic acid) or their alkali metal salts, trimethylacetic acid, p-toluenesulfonic acid, sodium silicate, acetone, sodium fluoride, cyanamide or ascorbic acid and/or a nitrogen-containing aromatic heterocycle, e.g. imidazole, N-methylimidazole, pyridine, pyrazole, pyrrole or 1,3,4-triazole.

When hydrogen peroxide or a compound liberating hydrogen peroxide is used as oxidizing agent it may also be advantageous to carry out the process according to the invention additionally in the presence of small amounts (generally up to 1% of the weight of the reactants) of a defoamer and deaerator in order to improve removal of the oxygen produced in the reaction. Examples of suitable compounds of this type are long-chain alcohols of phosphoric esters.

When hydrogen peroxide or a compound liberating hydrogen peroxide is used as oxidizing agent it may also be advantageous to carry out the process according to the invention additionally in the presence of from 0.1 to 10 mol %, preferably 1 to 10 mol %, based on phenol II, of benzoic acid, m-chlorobenzoic acid, phosphorous acid, nitrous acid or a nitrite, preferably an alkali metal nitrite. It is possible in this way to reduce both the reaction temperature (20° to 60° C., preferably 30° to 50° C.) and the amount of hydrogen peroxide or compound liberating hydrogen peroxide.

It may additionally be advantageous to carry out the process in the presence of small amounts of sulfuric acid, as a rule from 0.1 to 2% by weight of concentrated sulfuric acid based on the weight of diluent. It is possible in this way to increase the yield of benzoquinones I.

As a rule, from 1 to 10 mol, preferably 1 to 6 mol and, in particular, 1.5 to 5 mol of hydrogen peroxide, from 1 to 5 mol, preferably 1 to 3 mol and, in particular, 1.2 to 2.5 mol of organic hydroperoxide or from 1 to 5 mol, preferably 1 to 4 mol of percarboxylic acid (in each case based on one peroxycarboxyl radical) or from 1 to 3 mol, preferably 1.2 to 2.5 mol of peroxomonosulfuric acid or its salts are used per mol of phenol of the formula II.

The oxygen-transferring catalyst which contains a heavy metal ion bound in a complex is generally used in an amount of from 0.1 to 5 mol %, preferably 1 to 3 mol %, based on the phenol II.

Examples of suitable diluents are water, acetic acid, chloroform, toluene, N,N-dimethylformamide, N-methylpyrrolidone, alcohols such as methanol, ethanol, propanol, isopropanol, butanol or isobutanol, glycols such as ethylene glycol or propylene glycol, or mixtures thereof.

Acetic acid or mixtures of water and acetic acid are preferably used.

Two-phase mixtures resulting, for example, from use of water and a solvent which is immiscible or has only limited miscibility with water are, where appropriate, provided with a phase-transfer catalyst. Suitable phase-transfer catalysts in this case are the conventional products such as arylsulfonates, e.g. benzene- or toluenesulfonate.

The novel process is, as a rule, carried out under atmospheric pressure and at from 0° to 100° C., preferably from 20° to 60° C. It can be carried out either continuously or batchwise.

The novel process is expediently carried out in such a way that first the catalyst, preferably dissolved in the diluent, and, where appropriate, the auxiliaries are introduced and then, preferably simultaneously, a solution of the phenol II in the diluent, in the presence or absence of an acid, and the oxidizing agent are added with stirring.

However, it is also possible to introduce the catalyst and phenol II together with the diluent and then to add the oxidizing agent with stirring.

As a rule, the ratio by weight of phenol II to diluent for this is from 1:3 to 1:40, preferably from 1:3 to 1:10.

The oxidation takes place with stirring at the abovementioned temperature. The reaction is generally complete after addition of the oxidizing agent. The target product can then be isolated in a conventional way, e.g. by steam distillation or by filtration.

The process according to the invention is simple to carry out and provides the benzoquinones of the formula I in good yield and high purity.

The benzoquinones of the formula I are valuable intermediates for preparing active substances, e.g. α-tocopherol (vitamin E).

The following examples are intended to illustrate the invention further.

EXAMPLE 1

A solution of 13.6 g (100 mmol) of 2,3,6-trimethylphenol in 40 ml of acetic acid and 62.3 g (550 mmol) of 30% by weight aqueous hydrogen peroxide were simultaneously added dropwise to a stirred solution of 0.68 g (2.0 mmol) of iron 5,14-dihydrodibenzo[b,i][5,9,14,18]tetraaza[14]annulene, 2.52 g (2.0 mmol) of a 40% by weight aqueous solution of a pentasodiumdiethylenetriaminepentaacetate and 0.5 ml of concentrated sulfuric acid in 50 ml of acetic acid at 40° C. with cooling. The reaction mixture was then subjected to steam distillation. The distillate was extracted by shaking with methylene chloride. The organic phase was shaken with aqueous sodium bicarbonate solution and then with water, separated from the aqueous phase, dried over magnesium sulfate, filtered and concentrated to a yellow oil, which slowly solidifed. 12.6 g (84%) of 2,3,5-trimethyl-p-benzoquinone were obtained in the form of yellow oily crystals.

EXAMPLE 2

A solution of 13.6 g (100 mmol) of 2,3,6-trimethylphenol in 40 ml of acetic acid and a solution of 32.3 g (250 mmol) of 70% by weight aqueous tert-butyl hydroperoxide in 20 ml of acetic acid were simultaneously added dropwise to a stirred solution of 0.68 g (2.0 mmol) of iron 5,14-dihydrodibenzo[b,i][5,9,14,18]tetraaza[14]annulene and 0.5 ml of concentrated sulfuric acid in 50 ml of acetic acid at 40° C. with cooling. The reaction mixture was then subjected to steam distillation. The distillate was extracted by shaking with methylene chloride. The organic phase was shaken with aqueous sodium bicarbonate solution and then with water, separated from the aqueous phase, dried over magnesium sulfate, filtered and concentrated to a yellow oil, which slowly solidifed. 14.0 g (93%) of 2,3,5-trimethyl-p-benzoquinone were obtained in the form of yellow oily crystals.

EXAMPLE 3

A solution of 13.6 g (100 mmol) of 2,3,6-trimethylphenol in 40 ml of acetic acid and a solution of 73.7 g (240 mmol) of 50% by weight potassium peroxomonosulfate in 320 ml of water were simultaneously added dropwise to a stirred solution of 0.68 g (2.0 mmol) of iron 5,14-dihydrodibenzo[b,i][5,9,14,18]tetraaza[14]annulene and 0.5 ml of concentrated sulfuric acid in 50 ml of acetic acid at room temperature with cooling. The reaction mixture was then subjected to steam distillation. The distillate was extracted by shaking with methylene chloride. The organic phase was shaken with aqueous sodium bicarbonate solution and then with water, separated from the aqueous phase, dried over magnesium sulfate, filtered and concentrated to a yellow oil, which slowly solidifed. 11.1 g (74%) of 2,3,5-trimethyl-p-benzoquinone were obtained in the form of yellow oily crystals.

EXAMPLE 4

A solution of 15.2 g (100 mmol) of 2,3,6-trimethylhydroquinone in 150 ml of acetic acid and a 28.4 g (250 mmol) of 30% by weight aqueous hydrogen peroxide were simultaneously added dropwise to a stirred solution of 0.68 g (2.0 mmol) of iron 5,14-dihydrodibenzo[b,i][5,9,14,18]tetraaza[14]annulene, 2.52 g (2.0 mmol) of a 40% by weight aqueous solution of pentasodium diethylenetriaminepentaacetate and 0.5 ml of concentrated sulfuric acid in 50 ml of acetic acid at 40° C. with cooling. The reaction mixture was then subjected to steam distillation. The distillate was extracted by shaking with methylene chloride. The organic phase was shaken with aqueous sodium bicarbonate solution and then with water, separated from the aqueous phase, dried over magnesium sulfate, filtered and concentrated to a yellow oil, which slowly solidifed. 12.9 g (86%) of 2,3,5-trimethyl-p-benzoquinone were obtained in the form of yellow oily crystals.

EXAMPLE 5

A solution of 15.2 g (100 mmol) of 2,3,5-trimethylhydroquinone in 150 ml of acetic acid and 16.1 g (125 mmol) of 70% by weight aqueous tert-butyl hydroperoxide were simultaneously added dropwise to a stirred solution of 0.68 g (2.0 mmol) of iron 5,14-dihydrodibenzo[b,i][5,9,14,18]tetraaza[14]annulene and 0.5 ml of concentrated sulfuric acid in 50 ml of acetic acid at 40° C. with cooling. The reaction mixture was then subjected to steam distillation. The distillate was extracted by shaking with methylene chloride. The organic phase was shaken with aqueous sodium bicarbonate solution and then with water, separated from the aqueous phase, dried over magnesium sulfate, filtered and concentrated to a yellow oil, which slowly solidifed. 11.7 g (78%) of 2,3,5-trimethyl-p-benzoquinone were obtained in the form of yellow oily crystals.

EXAMPLE 6

28.4 g (250 mmol) of 30% by weight aqueous hydrogen peroxide are added dropwise to a stirred solution of 12.2 g (50 mmol) of 2,6-dimethylphenol, 0.34 g (1.0 mmol) of iron 5,14-dihydrodibenzo[b,i][5,9,14,18]tetraaza[14]annulene, 1.26 g (1.0 mmol) of a 40% by weight aqueous solution of pentasodium diethylenetriaminepentaacetate and 0.5 ml of concentrated sulfuric acid in 50 ml of acetic acid at 40° C. with cooling. After cooling to room temperature, the solid was filtered off and recrystallized from acetic acid to yield 7.4 g (62%) of 3,3',5,5'-tetramethyldiphenoquinone in the form of dark red needles. Melting point 207°–225° C. (decomposition).

EXAMPLE 7

A solution of 11.4 g (100 mmol) of hydroquinone in 250 ml of acetic acid and 28.4 g (250 mmol) of 37% by weight aqueous hydrogen peroxide were simultaneously added dropwise to a stirred solution of 0.68 g (2.0 mmol) of iron 5,14-dihydrodibenzo[b,i][5,9,14,18]-tetraaza[14]annulene, 2.52 g (2.0 mmol) of a 40% by weight aqueous solution of pentasodium diethylenetriaminepentaacetate and 0.5 ml of concentrated sulfuric acid in 50 ml of acetic acid at 40° C. with cooling. The mixture was then stirred for 15 min and subsequently subjected to a steam distillation. The distillate was extracted three times with a total of 750 ml of methylene chloride. The organic phase was shaken with aqueous sodium bicarbonate solution and then with water, separated from the aqueous phase, dried over magnesium sulfate, filtered and evaporated to dryness to yield 6.8 g (63%) of benzoquinone in the form of a yellow powder. Melting point 113°–115° C.

EXAMPLE 8

A solution of 12.4 g (100 mmol) of methylhydroquinone in 90 ml of acetic acid and 28.4 g (250 mmol) of 30% by weight aqueous hydrogen peroxide were simultaneously added dropwise to a stirred solution of 0.68 g (2.0 mmol) of iron 5,14-dihydrodibenzo[b,i]-[5,9,14,18]tetraaza[14]annulene, 2.52 g (2.0 mmol) of a 40% by weight aqueous solution of pentasodium diethylenetriaminepentaacetate and 0.5 ml of concentrated sulfuric acid in 50 ml of acetic acid at 40° C. with cooling. The mixture was then stirred for 15 min and subsequently subjected to a steam distillation. The distillate was extracted three times with a total of 400 ml of methylene chloride. The organic phase was shaken with aqueous sodium bicarbonate solution and then with water, separated from the aqueous phase, dried over magnesium sulfate, filtered and evaporated to dryness to yield 10.9 g (89%) of methylbenzoquinone in the form of a yellow powder. Melting point 69°–71° C.

EXAMPLE 9

A solution of 13.8 g (100 mmol) of 2,3-dimethylhydroquinone in 500 ml of acetic acid and 28.4 g (250 mmol) of 30% by weight aqueous hydrogen peroxide were simultaneously added dropwise to a stirred solution of 0.68 g (2.0 mmol) of iron 5,14-dihydrodibenzo[b,i][5,9,14,18]tetraaza[14]annulene, 2.52 g (2.0 mmol) of a 40% by weight aqueous solution of pentasodium diethylenetriaminepentaacetate and 0.5 ml of concentrated sulfuric acid in 50 ml of acetic acid at 40° C. with cooling. The mixture was then stirred for 15 min and subsequently subjected to a steam distillation. The distillate was extracted three times with a total of 400 ml of methylene chloride. The organic phase was shaken with aqueous sodium bicarbonate solution and then with water, separated from the aqueous phase, dried over magnesium sulfate, filtered and evaporated to dryness to yield 11.8 g (87%) of 2,3-dimethylbenzoquinone in the form of a yellow powder. Melting point 57°–59° C.

EXAMPLE 10

34.6 g (100 mmol) of dipotassium 2,5-dihydroxybenzene-1,4-disulfonate were dissolved in 500 ml of water at 60° C. After addition of 0.68 g (2 mmol) of iron 5,14-dihydrodibenzo[b,i][5,9,14,18]-tetraaza[14]annulene, 0.8 g (2 mmol) of diethylenetriaminepentaacetic acid, 1 ml of concentrated sulfuric acid and 1 ml of a commercial antifoam agent, 28.4 g (250 mmol) of 30% by weight aqueous hydrogen peroxide were added dropwise. The mixture was stirred for 15 min at 60° C. The solution was cooled to 5°–10° C. and then the solid was filtered off with suction and recrystallized from water to yield 14.5 g (42%) of dipotassium 1,4-benzoquinone-2,5-disulfonate in the form of reddish brown needles. Melting point >360° C.

EXAMPLE 11

Oxygen was passed into a solution of 0.68 g (2 mmol) of iron 5,14-dihydrodibenzo[b,i][5,9,14,18]tetraaza[14]annulene in 150 ml of 85% by weight aqueous acetic acid and, during this, a solution of 13.6 g (100 mmol) of 2,3,6-trimethylphenol and 0.5 g of concentrated sulfuric acid in 75 ml of 85% by weight acetic acid was added dropwise while stirring vigorously at 40° C. After oxygen uptake ceased, the mixture was subjected to a steam distillation. The distillate was extracted with tert-butyl methyl ether. The organic phase was shaken with aqueous sodium bicarbonate solution and then with water, separated from the aqueous phase, dried over magnesium sulfate, filtered and evaporated to dryness to yield 12.0 g (80%) of 2,3,5-trimethylbenzoquinone in the form of yellow oily crystals.

EXAMPLE 12

Oxygen was passed into a solution of 0.68 g (2 mmol) of iron 5,14-dihydrodibenzo[b,i][5,9,14,18]tetraaza[14]annulene in 150 ml of 85% by weight aqueous acetic acid and, during this, a solution of 11.0 g (100 mmol) of hydroquinone and 0.5 g of concentrated sulfuric acid in 75 ml of 85% by weight acetic acid was added dropwise while stirring vigorously at 40° C. After oxygen uptake ceased, the mixture was subjected to a steam distillation. The distillate was extracted with tert-butyl methyl ether. The organic phase was shaken with aqueous sodium bicarbonate solution and then with water, separated from the aqueous phase, dried over magnesium sulfate, filtered and evaporated to dryness to yield 5.0 g (46%) of benzoquinone in the form of a yellow powder. Melting point 109°–110° C.

EXAMPLE 13

Oxygen was passed into a solution of 0.68 g (2 mmol) of iron 5,14-dihydrodibenzo[b,i][5,9,14,18]tetraaza[14]annulene in 150 ml of 85% by weight aqueous acetic acid and, during this, a solution of 12.4 g (100 mmol) of methylhydroquinone and 0.5 g of concentrated sulfuric acid in 75 ml of 85% by weight acetic acid was added dropwise while stirring vigorously at 40° C. After oxygen up-take ceased, the mixture was subjected to a steam distillation. The distillate was extracted with tert-butyl methyl ether. The organic phase was shaken with aqueous sodium bicarbonate solution and then with water, separated from the aqueous phase, dried over magnesium sulfate, filtered and evaporated to dryness to yield 7.5 g (46%) of 2-methylbenzoquinone in the form of a yellow powder. Melting point 66°–68° C.

EXAMPLE 14

Oxygen was passed into a solution of 0.68 g (2 mmol) of iron 5,14-dihydrodibenzo[b,i][5,9,14,18]tetraaza[14]annulene and 0.5 g of concentrated sulfuric acid in 150 ml of 85% by weight aqueous acetic acid and, during this, a solution of 12.4 g (100 mmol) of 2,3-dimethylhydroquinone in 75 ml of 85% by weight acetic acid was added dropwise while stirring vigorously at 40° C. After oxygen uptake ceased, the mixture was subjected to a steam distillation. The distillate was extracted with tert-butyl methyl ether. The organic phase was shaken with aqueous sodium bicarbonate solution and then with water, separated from the aqueous phase, dried over magnesium sulfate, filtered and evaporated to dryness to yield 13.0 g (95%) of 2,3-dimethylbenzoquinone in the form of a yellow powder. Melting point 56°–57° C.

We claim:

1. A process for preparing benzoquinones of the formula I

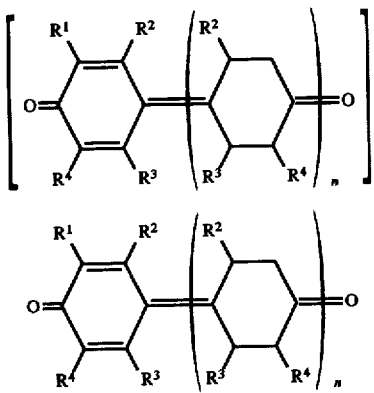

where R, $R^2$, $R^3$ and $R^4$ are, independently of one another, each hydrogen, $C_1$–$C_4$-alkyl, $C_1$–$C_4$-alkoxy, aryloxy, $C_1$–$C_4$-alkylsulfonyl, arylsulfonyl, hydroxysulfonyl, hydroxyl or halogen, and n is 0 or 1, by oxidizing a phenol of the formula II

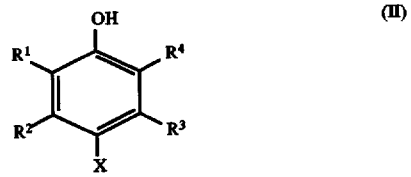

where X is hydrogen or hydroxyl, and $R^1$, $R^2$, $R^3$ and $R^4$ each have the above-mentioned meanings, using an oxidizing agent selected from the group consisting of oxygen, hydrogen peroxide, a compound which liberates hydrogen peroxide, an organic hydroperoxide, a percarboxylic acid or peroxomonosulfuric acid or salts thereof in the presence of a diluent containing acid other than the recited reactants and from about 0.1 to 5 mol % based on the phenol of formula II of an oxygen-transferring catalyst selected from the group consisting of iron, manganese and chromium dihydrodibenzotetraaza(14)annulenes.

2. A process as claimed in claim 1, wherein n is 0.

3. A process as claimed in claim 1, wherein $R^1$, $R^2$, $R^3$ and $R^4$ are, independently of one another, each hydrogen, $C_1$–$C_4$-alkyl or hydroxysulfonyl.

4. A process as claimed in claim 1, wherein $R^1$, $R^2$, $R^3$ and $R^4$ are, independently of one another, each hydrogen or methyl.

5. A process as claimed in claim 1, wherein $R^1$, $R^2$ and $R^3$ are each methyl and $R^4$ is hydrogen.

6. The process of claim 1, where the diluent is acetic acid.

7. The process of claim 1, where the diluent is a mixture of water and acetic acid.

8. The process of claim 1, where the oxygen transferring catalyst is selected from the group consisting of iron, manganese and chromium unsubstituted dihydrodibenzotetraaza (14) annulenes.

9. The process of claim 8, where the oxygen-transferring catalyst is iron 5,14-dihydrodibenzo(b,i)(5,9,14,18)tetraaza (14)annulene.

10. A process as claimed in claim 1, wherein the oxygen-transferring catalyst is an iron dihydrodibenzotetraaza(14) annulene.

* * * * *